United States Patent
Manzur et al.

(10) Patent No.: US 9,219,890 B1
(45) Date of Patent: Dec. 22, 2015

(54) OPTICAL SURFACE ANALYSIS SYSTEM AND METHOD

(75) Inventors: Tariq Manzur, Lincoln, RI (US); John W. Zeller, Middletown, CT (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 655 days.

(21) Appl. No.: 13/591,871

(22) Filed: Aug. 22, 2012

(51) Int. Cl.
*H04N 7/18* (2006.01)
*H04N 1/06* (2006.01)
*G01N 21/88* (2006.01)

(52) U.S. Cl.
CPC ..................... *H04N 7/183* (2013.01)

(58) Field of Classification Search
CPC ....................................... H04N 7/183
See application file for complete search history.

(56) References Cited

U.S. PATENT DOCUMENTS

| 6,807,022 B1* | 10/2004 | Yanowitz | ................ 359/822 |
| 2001/0030744 A1* | 10/2001 | Chang | ................ 356/237.3 |
| 2013/0002849 A1* | 1/2013 | Sakai et al. | ................ 348/86 |

* cited by examiner

*Primary Examiner* — Jefferey Harold
*Assistant Examiner* — Justin Sanders
(74) *Attorney, Agent, or Firm* — James M. Kasischke; Michael P. Stanley

(57) ABSTRACT

An image analysis system and method are provided. The system can include a base for receiving an optical surface, at least one light source positioned above and at an oblique angle with respect to the optical surface, a camera positioned above the optical surface and adapted to provide an image data indicative of an image of the optical surface, and a computerized system adapted to receive the image data from the camera. The computerized system can analyze the image data to identify and quantify surface defects. Classification identifiers can be assigned to each surface defect based on the physical characteristics of the surface defect. A transmission metric is calculated for the optical surface to allow objective judgment of the surface.

20 Claims, 4 Drawing Sheets

OPTICAL SURFACE ANALYSIS SYSTEM AND METHOD

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention relates to an optical surface analysis system and method.

(2) Description of the Prior Art

An optical surface may include any surface allowing the transmission of and/or refraction of light. A curved surface describes a lens generally understood to be an optical device that transmits and/or refracts light that passes through it. The lens may converge or diverge the light passing through. Exemplary types of lenses include, but are not limited to, biconvex, biconcave, plano-convex, positive meniscus, negative meniscus, plano-concave, etc. Other types of optical surfaces include those with a flat surface. An example of a flat window surface is a periscope head window or other types of optical glass.

During normal use, the optical surface may be subjected to environmental or operational circumstances that damage it. One common form of damage includes surface defects, e.g., the optical surface may become scratched, gouged, pitted, etc. These surface defects interact with the light passing through the optical surface, thereby distorting the light, and consequently an image of the object on the opposing side. That is, a user viewing an object through an optical surface may have difficulty discerning the object clearly because of the distortions caused by the surface defects. In the case of a periscope head window, surface defects are particularly problematic because almost all objects viewed are located at great distances.

A number of prior art systems have attempted to analyze optical surfaces. In one common procedure, technicians survey the optical surface and, if significant defects are found, it is considered to be in need of replacement. This method is very subjective and often results in the optical surface being replaced, which can be cost prohibitive.

As another example, U.S. Pat. No. 8,049,879, issued to Shetterly et al. teaches an apparatus for measuring transmitted optical distribution on glass sheets. Broadly, Shetterly et al. teach projecting a light source through the glass sheet and onto a known background image having a known pattern (e.g., a series of dots). Shetterly et al., however, does not generally disclose the inventive aspects of the present disclosure.

Thus, there is a need to for an improved system and method to analyze optical surfaces, such as is identified in the present disclosure.

SUMMARY OF THE INVENTION

Accordingly, it is an object of the present invention to provide a method of analyzing optical surfaces. The method may comprise receiving, via a first communication channel, image data indicative of an image of an optical surface. The method may also comprise executing an analysis module on a computerized system to analyze the image data to identify a surface defect, the analysis module further adapted to determine a physical characteristic for each surface defect and assign a classification identifier to each surface defect based on the physical characteristics of the surface defect. The method may further comprise executing a calculation module on the computerized system to calculate transmission data for the optical surface based on the classification identifiers assigned to each surface defect. The method may even further comprise executing a comparison module on the computerized system to compare the transmission data to a predetermined criteria, and further to provide an output to a user identifying whether the transmission data meets the predetermined criteria.

Another object of the present invention is to provide another method of analyzing an optical surface. The method may comprise receiving, via a first communications channel, image data indicative of an image of an optical surface. The method may also comprise executing an analysis module on a computerized system to analyze the image data to identify a surface defect on the optical surface, determine a position on the optical surface the defect is located, and determine a physical characteristic for each surface defect, the analysis module further adapted to assign a classification identifier to each surface defect based on the physical characteristic of the surface defect. The method may further comprise executing a calculation module on the computerized system to calculate transmission data and scattering data for each of a plurality of sections of the optical surface, the transmission data and scattering data for each section based on the classification identifiers assigned to each surface defect positioned within the section. The method may even further comprise executing a comparison module on the computerized system to compare the transmission data and the scattering data to a predetermined criteria to identify whether the transmission data and scattering data meets the predetermined criteria.

Yet another object of the present invention is to provide an optical surface analysis system. The system may comprise a base adapted to receive a flat or curved optical surface, at least one light source positioned above and at an oblique angle with respect to the optical surface received in the base, a camera positioned above the optical surface, the camera adapted to provide an image data indicative of an image captured of the optical surface and focused so to be able to adequately resolve surface defects, and a computerized system adapted to receive the image data from the camera. The computerized system may comprise a processor and a memory module storing computer executable code that, when executed by the processor, causes the computerized system to perform aspects of the present disclosure. The computer executable code may cause the computerized system to analyze the image data to identify and quantify a physical characteristic of a surface defect on the optical surface, to assign a classification identifier to each surface defect based on the physical characteristics of the surface defect, and to calculate transmission data for the optical surface based on the classification identifiers assigned to each surface defect.

Other objects, features, and advantages of the present invention will be apparent to those having ordinary skill in the art reading the instant specification, drawings, and appended claims.

DETAILED DESCRIPTION OF THE INVENTION

Figure 1:
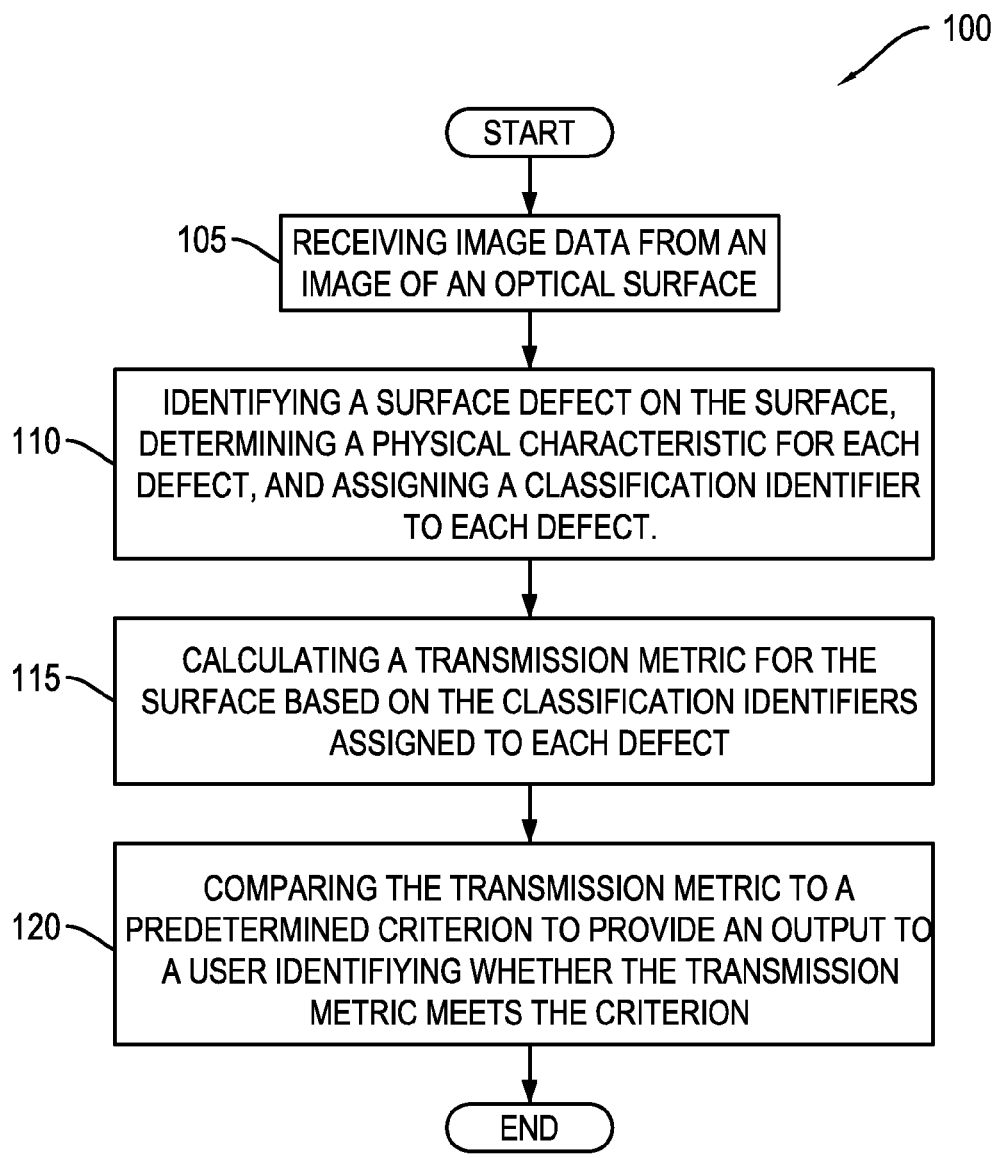
FIG. 1 is a flowchart of an exemplary method of analyzing an optical lens, in accordance with aspects of the present disclosure.

Referring now to the drawings, and more particularly to FIG. 1, shown therein is a flowchart of an exemplary method 100 of analyzing an optical surface, in accordance with aspects of the present disclosure. The method 100 may be used to objectively analyze and evaluate an optical surface to determine if the optical surface is suitable for continued use or needs to be replaced. The method 100 is a computer-implemented method. The method 100 includes a step 105 of receiving image data. The image data is indicative of an image of an optical surface. The image data can be received via a first communication channel, e.g., via a wired or wireless communications medium, conductor, transmitter, etc. The image data can be received from a camera capturing an image of the optical surface to be analyzed. Certain aspects may provide for the camera to be a digital camera that may interface with a computerized system adapted to perform or carry out at least portions of the presently disclosed inventive concept.

The method 100 further includes a step 110 of analyzing the image data to identify a surface defect on the optical surface. The step 110 may be executed via an analysis module on a computerized system. The analysis module may be further adapted or configured to determine a physical characteristic for each surface defect. In one embodiment this analysis module can be realized as MATLAB™ or other computer code executable on a general purpose computer. Once the surface defect has been characterized, the analysis module assigns a classification identifier to the surface defect. The classification identifier may be based on the physical characteristics of the surface defect. Thus each surface defect identified on the optical surface can be assigned a classification identifier dependent upon the physical characteristics of the surface defect. As one example the classification identifier can be dependent on the length of the surface defect, the width of the surface defect, the length/width ratio of the surface defect, and/or the depth of the surface defect, and/or the height of the surface defect on the optical surface. In accordance with certain aspects of the present disclosure, the classification identifier can be selected or otherwise correspond to a scratch and dig number as defined by U.S. Military Specification for the Inspection of Optical Components, MIL-O-13830A.

The method 100 can further include a step 115 of calculating a transmission metric for the optical surface. The transmission metric is calculated based on the classification identifiers assigned to each surface defect. In accordance with certain aspects, the transmission metric can be indicative of the optical transmission parameters associated with the optical surface as affected by the surface defects. For example, the number of inclusive defects can be counted and the defect density can also be calculated for the optical surface. This information can be used to calculate or otherwise determine the transmission characteristics of the optical surface.

The method 100 can further include a step 120 of comparing the transmission data to predetermined criteria. The predetermined criteria can be user selectable criteria by which the optical surface can be determined as operational or in need of replacement. Step 120 can be executed via a comparison module on the computerized system. The predetermined criteria (pass/fail criteria) can be based on user supplied parameters, data from a lookup table, or the manufacturer of the optical surface. Possible parameters include transmission data or coefficient, scattering data or coefficient, number of surface defects, and/or density of surface defects, etc. Other parameters can also be used. As one example, the manufacturer of an optical surface may provide a transmission data or coefficient for the optical surface, wherein when the calculated transmission data indicates a reduction of the transmission properties of the optical surface of 10%, 20%, 30%, etc., the optical surface can be determined unserviceable and in need of replacement.

In accordance with other aspects, the method 100 can be further configured to, via for example the comparison module on the computerized system, to provide an output to a user of the computerized system identifying whether the transmission data for the optical surface meets the predetermined criteria. For example, the comparison module can provide an output to a user in the form of a graphical user interface (GUI), a histogram plot displayed on a monitor or screen, or alternately in a hard copy via a printout, wherein the user can be notified whether the optical surface continues to be operational or is in need of replacement, based on the surface defects.

In accordance with other aspects, the method 100 can further be adapted to subdivide the optical surface into a plurality of sections, e.g., in the case of a flat surface such as a periscope head window. The sections may correspond to differing viewing areas of the optical surface. The calculation module may further calculate the transmission metric for the plurality of sections of the optical surface based on the classification identifiers assigned to each surface defect within each section. The various sections can be assigned a weighted value based on their relative effect on optical transmission; for example, surface defects in a section near the center of the optical surface may generally affect the overall quality of optical transmission more than surface defects located near the perimeter. The transmission data for each section may correspond to a plurality of viewing areas for the optical surface.

In accordance with other aspects, the computerized system can further include a memory module wherein previous transmission metrics, either calculated beforehand with regards to the optical surface being tested or provided by the manufacturer of the optical surface, can be stored. The transmission metric calculated via the method 100 may further be compared to the previous transmission data so as to calculate and determine the impact the surface defects have on the optical surface since the previous test, i.e., to determine the amount of degradation of the optical surface. Comparing the calculated transmission data from the method 100 with previous transmission metrics regarding that optical surface may provide valuable lifecycle data for the surface.

Figure 2:
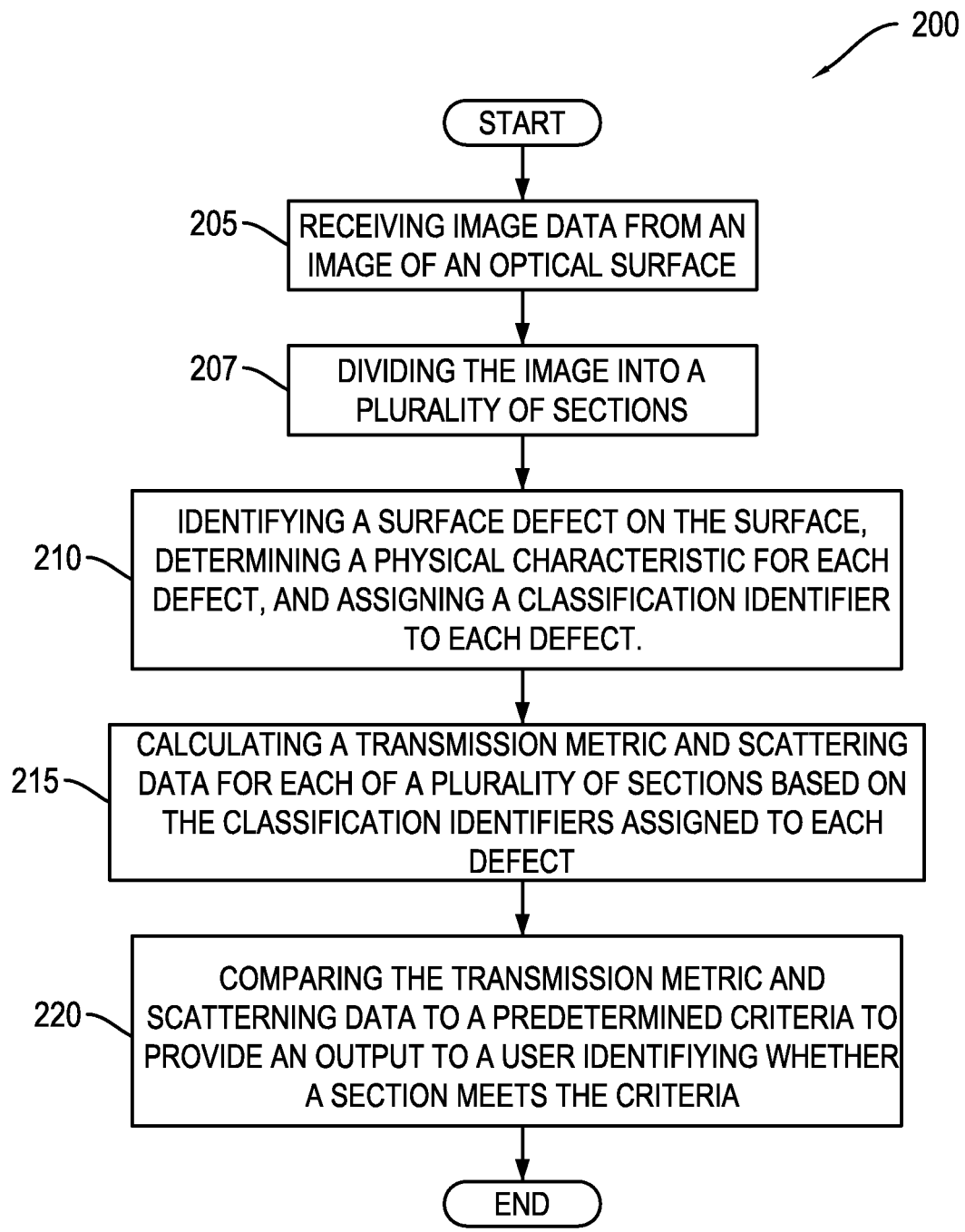
FIG. 2 is a flowchart of another exemplary method of analyzing an optical lens, in accordance with aspects of the present disclosure.

Referring to FIG. 2 now shown therein is another exemplary method 200 of analyzing an optical surface. The method 200 is similar to the method 100 discussed above except wherein additional information is provided. The method 200 may comprise a step 205 of receiving image data indicative of an image of an optical surface. Again the image data can be received via a first communications channel and provided by a digital camera.

The method 200 can further include a step 210 of analyzing the image data to identify surface defect on the optical surface. Step 210 can be accomplished via executing an analysis module on a computerized system. The analysis module may further determine a position or location on the optical surface where the surface defect is located and further to determine the physical characteristic for each of the surface defects. That is, the analysis module analyzes the image data of the optical surface so as to generate a map of the surface area of the optical surface, identify and locate each of the surface defects on the optical surface, and further to determine the physical characteristics for each of the surface defects, e.g., the length, width, depth, and/or height of the surface defects. The analysis module may further be configured to assign a classification identifier to each surface defect. The classification identifier can be based on the physical characteristics of the surface defect, such as the length/width ratio. Again, the classification identifier may correlate to the scratch and dig numbers in accordance with MIL-O-13830A or a similar standard.

The method 200 can further include a step 215 of calculating a transmission metric and scattering data for each of the plurality of sections of the optical surface. The step 215 can be accomplished via a calculation module operating on the computerized system. The transmission metric and scattering data can be calculated based on the classification identifiers assigned to each of the surface defects positioned within each section. That is, step 215 calculates the transmission metric and the scattering data for each section of the optical surface such that, for example, a user observing an object through a particular section of the optical surface can determine which section might provide the optimal viewing. The transmission metric and also the scattering data may generally include information indicative of the manner in which light is transmitted through the optical surface or scattered by the optical surface via, for example, the surface defects.

The method 200 can further include a step 220 of comparing the transmission metric and scattering data to a predetermined criteria to identify whether the transmission metric and the scattering data meets the predetermined criteria. The step 220 can be accomplished via executing a comparison module on the computerized system. Certain aspects may provide for the computerized system to provide an output to a user indicating whether the transmission metric and/or the scattering data meet the predetermined criteria.

In accordance with even further aspects, the method 200 can also include a step of providing a simulation to a user wherein the simulation represents the degree that the surface defects will affect the transmission properties of the optical surface. That is, the computerized system may execute a simulation module to provide the simulation output to the user. The simulation output can provide a visual indicator of the effects due to scattering caused by the surface defects simulating the impact the level of surface defects has on imaging performance. That is, the optical scattering caused by defects at the image plane in the optical surface effectively blurs the images seen through the surface. Based on the calculated transmission data and/or scattering data, an image representing one that would be captured through the surface is blurred using the computerized system (e.g., a software algorithm employing a blur filter) to simulate the corresponding view through that surface to the user. The simulation output can further aid in determining whether the optical surface meets operational requirements or needs to be replaced.

Additional aspects can provide for the method 200 to receive a plurality of image data indicative of multiple images of the optical surfaces. The method 200 can assign the classification identifiers to each surface defect for each image data. The transmission data and/or the scattering data can be calculated based on an average, medium, or mean of the classification identifiers assigned to each surface defect for each image data. Performing the method 200 on a plurality of images of the optical surface and then assigning the classification identifier based on the average of the surface defects identified using the method 200 may provide for improved accuracy.

Figure 3:
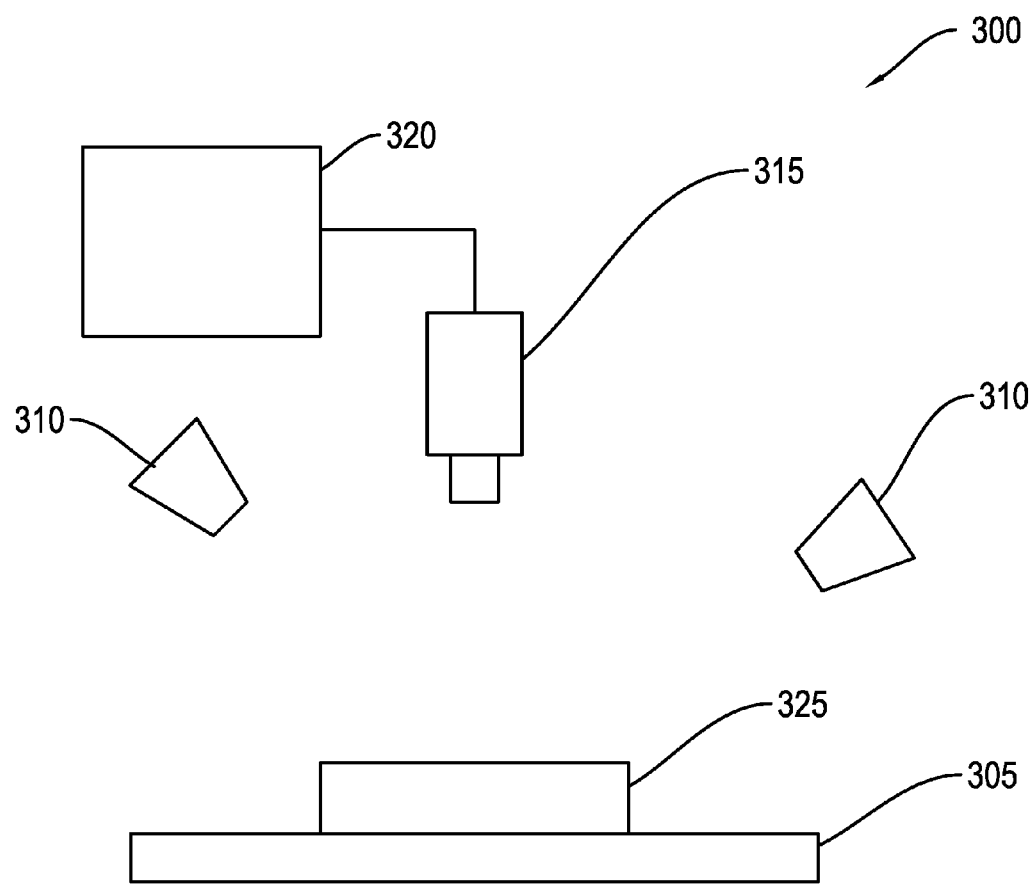
FIG. 3 is a block diagram of an exemplary optical lens analysis system constructed in accordance with aspects of the present disclosure.

Referring to FIG. 3 now, shown therein is a perspective view of an exemplary optical surface analysis system 300, constructed in accordance with the present disclosure. The system 300 comprises a base 305, at least one light source 310 (two being shown in FIG. 3 by way of example), a camera 315, and a computerized system 320. The base 305 can be adapted to receive an optical lens 325 (e.g., an optical surface). The base 305 can include a predefined pattern or measurement grid or may have a solid background color. The light source 310 can be a high intensity florescent lamp or a light-emitting diode (LED) array. As shown in FIG. 3, the light source 310 can include two light sources wherein each light source is positioned on different sides of the camera 315 so as to project light onto the optical lens 325 at differing angles. The angles provided by the light sources can be oblique with respect to the optical lens 325, which may help to optimize the contrast and make the surface defects more discernible.

The camera 315 can be positioned above the optical lens 325 so as to provide image data indicative of an image captured of the optical surface. That is, the camera 315 can be positioned nadir, for example, with respect to the optical lens 325. The camera 315 can be a high resolution digital camera. An 11 megapixel camera provides sufficiently high definition for these purposes. The resolution of the camera should be sufficiently high to capture the features of interest. The camera 315 may provide an output of image data.

The computerized system 320 can be adapted to receive the image data from the camera 315. The computerized system 320 includes a processor and a memory module storing computer executable code that, when executed by the processor, causes the computerized system to perform certain aspects of the present disclosure. The computerized system 320 can be in electrical communication with the camera 315 so as to receive the image data from the camera 315, to control the camera 315, and the like. The computerized system 320 can be in communication with the camera 315 via, for example, a digital cable, a wireless connection, and the like. Other aspects may provide for the computerized system 320 to be remote from the camera 315 such that the camera 315 is utilized to capture the image data of the optical surfaces and then be transported to the computerized system for subsequent analysis, e.g., using a form of portable memory media or device.

As discussed above, the computer executable code causes the computerized system to analyze the image data to identify and quantify a physical characteristic of a surface defect on the optical lens 325. The computerized system 320 analyzes the image data via for example a plurality of modules. The modules can be configured or otherwise adapted to identify each surface defect on the optical lens 325 based on the image data provided by the camera 315. The modules can further be configured or otherwise adapted to quantify each physical characteristic of the surface defect e.g., to determine the physical dimensions of the surface defect (length, width, depth, height, etc.).

The computer executable code instructs the computerized system 320 to assign a classification identifier to each surface defect based on the physical characteristics of the surface defect and further to calculate the transmission data for the optical surface based on the assigned classification identifiers.

Other aspects provide for the system 300 to include two light sources 310 wherein each light source 310 is positioned at different oblique angles with respect to the optical lens 325.

Even further aspects provide for the computerized system 320 having a simulation output to a user wherein the simulation output simulates the effects of the surface defects on a user viewing an object through the optical lens 325. It should be understood that the system of FIG. 3 could be modified to provide a system for analyzing optical surfaces in field locations without removing the optical components.

Figure 4:
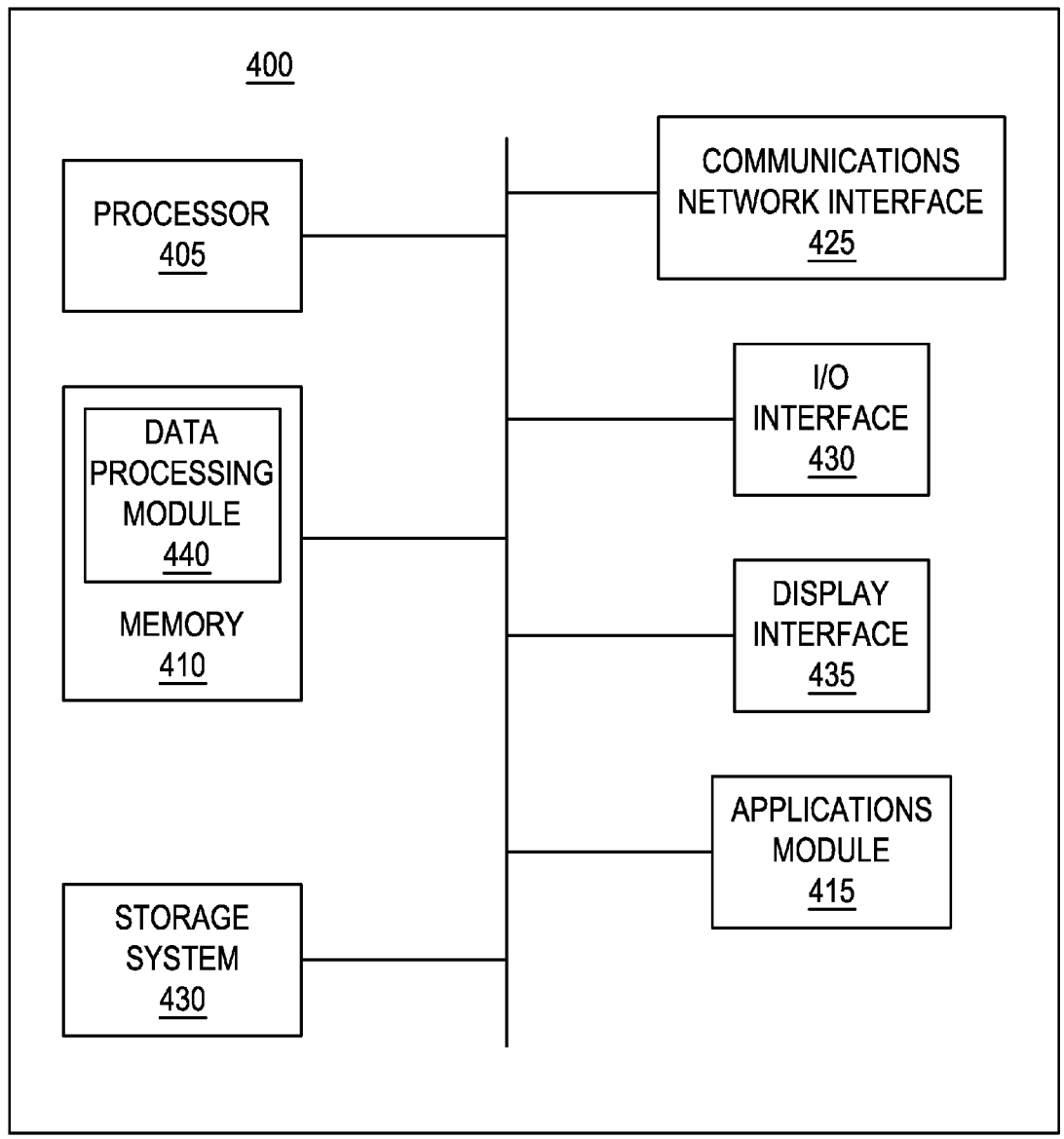
FIG. 4 is a block diagram of an exemplary computerized system in accordance with aspects of the present disclosure.

Referring now to FIG. 4, shown therein is an exemplary architecture of a computerized system 400 which can be adapted to practice aspects of the present disclosure, e.g., a computerized system 320. The exemplary architecture illustrated in FIG. 4 includes hardware, software, and/or combinations thereof, adapted to implement certain aspects of the presently disclosed and claimed inventive concept(s). The exemplary architecture is provided by way of example only and is not intended to be limiting. Changes and variations to the exemplary architecture illustrated in FIG. 4 providing similar functionality are considered within the scope of the present disclosure.

A module (or application), as referenced in the present invention, should be generally understood as a collection of routines that perform various system-level functions and can be dynamically loaded and unloaded by hardware and device drivers as required. The modular software components described herein may also be incorporated as part of a larger software platform or integrated as part of an application specific component.

The system 400 can include one or more processors 405 and memory 410. The memory 410 can store, in part, instructions and data for execution by the processor 405. The memory 410 can store executable code when in operation. The memory 410 can include a data processing module 440 for processing data. The system 400 can further include a storage system 415, communication network interface 425, input and output (I/O) interface(s) 430, and display interface 435. The components shown in FIG. 4 are depicted as being communicatively coupled via a bus 420. The components can be communicatively coupled via one or more data transport means. The communications network interface 425 can communicate with other digital devices (not shown) via a communications medium.

The memory and storage system of the system 400 can include a non-transitory computer-readable storage medium having stored thereon instructions executable by a processor to perform, at least partially, a computer-implemented method to analyze an optical surface, in accordance with the present disclosure. The instructions can include software used to implement modules discussed herein, and other modules.

I/O interfaces 430 can provide a portion of a user interface, receive audio input, and provide audio output. The I/O interface 430 can include component(s), logic instructions, and/or combinations thereof, adapted to permit the user to interface with the system 400. The I/O interfaces 430 can include an alpha-numeric keypad, such as a keyboard, for inputting alpha-numeric and other information, or a pointing device, such as a mouse, trackball, stylus, or cursor direction keys. The I/O interface 430 can further include a universal serial bus (USB) connection so as to permit electrical communication with a digital camera. The display interface 435 can include a liquid crystal display (LCD) or other suitable display device. The display interface 435 can receive textual and graphical information, and process the information for output to the display interface 435.

The system 400 can include any computerized system that can implement suitable applications adapted to carry out aspects of the present disclosure. Exemplary systems adapted to implement the system 400 include, but are not limited to, a general purpose computing system, a personal computer, a laptop computer, a netbook, a personal digital assistant (PDA), a smart phone, an e-reader, and/or equivalents thereof.

Broadly, the network discussed above can be adapted to provide a communications medium to permit one or more systems 400 to communicate with other systems 400, or a remote processing system (not shown), and vice versa. The network can be implemented via the World Wide Web (WWW), a wide area network (WAN), a local area network (LAN), the Internet, an intranet, a wireless network, a cellular telephone network, and/or equivalents or combinations thereof.

The system 400 can include component(s), logic instructions, and/or combinations thereof, adapted to implement at least a portion of the currently described and claimed inventive concept(s). The system 400 can include instructions stored on non-transitory computer readable medium that when executed causes the processing system to implement the present technology.

The system 400 can further include an applications module 445, which can include one or more of programs, applications, logic instructions, and computer executable code adapted to operate the system 400 as well as to carry out at least a portion of the currently described and claimed inventive concept(s).

It is to be understood that the description provided above regarding the particularities of the exemplary architecture implementing the system 400 is provided by way of example and is not to be considered limiting. The system 400 can be implemented as described above or with a variety of modifications and/or changes to the architecture without departing from the particular functions described herein. For example, the system 400 can be implemented as a stand-alone server, as a web server, as a distributed server system, as an application server, in combination with a database server, etc. When the system 400 is implemented as a webserver, the system 400 can communicate with other systems 400, via the network, through a series of web pages. The system 400 can be implemented as a single web server or as a distributed processing system including a plurality of server(s) coupled to one or more databases, either locally or remotely.

It will be understood that many additional changes in the details, materials, steps and arrangement of parts, which have been herein described and illustrated in order to explain the nature of the invention, can be made by those skilled in the art within the principle and scope of the invention as expressed in the appended claims.

The foregoing description of the preferred embodiments of the invention has been presented for purposes of illustration and description only. It is not intended to be exhaustive or to limit the invention to the precise form disclosed; and obviously many modifications and variations are possible in light of the above teaching. Such modifications and variations that would be apparent to a person skilled in the art are intended to be included within the scope of this invention as defined by the accompanying claims.

What is claimed is:

1. A method for analyzing an optical surface on a general purpose computer comprising:
receiving image data indicative of an image of an optical surface via a first communication channel;
analyzing the image data to identify a surface defect on the optical surface, the step of analyzing including determining a physical characteristic for each surface defect and assigning a classification identifier to each surface defect;

calculating a transmission metric for the optical surface based on the classification identifiers assigned to each surface defect;

comparing the calculated transmission metric to a predetermined criterion; and providing an output to a user identifying whether the transmission metric meets the predetermined criterion.

2. The method of claim 1 wherein the optical surface is a periscope head window.

3. The method of claim 1 further comprising the steps of: dividing the optical surface into a plurality of sections; and calculating the transmission metric for each of said plurality of sections based on the classification identifiers assigned to each surface defect within each section.

4. The method of claim 3 wherein each section corresponds to a viewing area of the optical surface.

5. The method of claim 1 wherein the classification identifier assigned to each surface defect is selected in accordance with an established standard.

6. The method of claim 1 wherein the output provided to the user is provided as a histogram plot showing groupings based on the classification identifier assigned to each surface defect.

7. The method of claim 1 wherein the transmission metric is further calculated based on a density of the surface defects on the optical surface.

8. The method of claim 1 further comprising the step of calculating scattering data indicative of the amount of light incident on the optical surface that is scattered and lost.

9. The method of claim 1 further comprising the step of comparing the calculated transmission metric calculated for the optical surface is further compared to a previously calculated transmission metric for said optical surface.

10. A method for analyzing an optical surface on a general purpose computer comprising:

receiving image data indicative of an image of an optical surface via a first communication channel;

dividing the optical surface into a plurality of sections; and analyzing the image data to identify a surface defect on the optical surface, the step of analyzing including determining a physical characteristic for each surface defect and assigning a classification identifier to each surface defect;

calculating a transmission metric for each of said plurality of sections based on the classification identifiers assigned to each surface defect within each section;

calculating scattering data for each of said plurality of sections indicative of the amount of light incident on the optical surface that is scattered and lost;

comparing the calculated transmission metric and the calculated scattering data to predetermined criteria; and providing an output to a user identifying whether the transmission metric and the scattering data meets the predetermined criteria.

11. The method of claim 10 further comprising the step of providing an output to a user simulating the effects the surface defects have on a predetermined image when viewed through the optical surface.

12. The method of claim 10 wherein the optical surface is a periscope head window.

13. The method of claim 10 wherein the classification identifier assigned to each surface defect is selected in accordance with an established standard.

14. The method of claim 10 wherein:

receiving image data comprises receiving data from a plurality of images indicative of the optical surface; and analyzing the image data further comprises assigning the classification identifiers to each surface defect for each image; and calculating a transmission metric includes calculating a transmission metric for each of the plurality of images and calculating an average transmission metric from the individual transmission metrics to use as the transmission metric;

calculating scattering data includes calculating scattering data for each of the plurality of images and calculating average scattering data from the individual scattering data to use as scattering data.

15. An image analysis system comprising:

a base adapted to receive an optical surface;

at least one light source positioned above and at an oblique angle with respect to the optical surface received in the base;

a camera positioned above the optical surface, the camera adapted to provide an image data indicative of an image captured of the optical surface; and a computerized system adapted to receive the image data from the camera, the computerized system further comprising a processor and a memory module storing computer executable code that, when executed by the processor, cause the computerized system to analyze the image data to identify and quantify a physical characteristic of a surface defect on the optical surface, to assign a classification identifier to each surface defect based on the physical characteristics of the surface defect, and to calculate transmission data for the optical surface based on the classification identifiers assigned to each surface defect.

16. The system of claim 15 further comprising at least two light sources positioned above the optical surface received in the base, wherein each light source is further positioned at different oblique angles with respect to the optical surface.

17. The system of claim 15 wherein the optical surface is a periscope head window.

18. The system of claim 15 wherein the computer executable code further causes the computerized system to receive a plurality of image data indicative of multiple images of the optical surface and assign the classification identifiers to each surface defect for each image data, and further to calculate the transmission data for the optical surface based on an average of the classification identifiers assigned to each surface defect.

19. The system of claim 15 wherein the computer executable code further causes the computerized system to compare the transmission data to a predetermined criteria and to output to a user information indicative of whether the transmission data meets the predetermined criteria.

20. The system of claim 15 wherein the computer executable code further causes the computerized system to provide a simulation output to a user simulating the effects the surface defects have on the user viewing an object through the optical surface.

* * * * *